(12) United States Patent
Ayalon et al.

(10) Patent No.: US 7,732,623 B2
(45) Date of Patent: *Jun. 8, 2010

(54) POLYMORPHIC FORM OF ATORVASTATIN CALCIUM

(75) Inventors: Ari Ayalon, Haifa (IL); Michal Levinger, Nofit (IL); Sofia Roytblat, Haifa (IL); Valerie Niddam, Even-Yeouda (IL); Revital Lifshitz, Herzilia (IL); Judith Aronhime, Rechovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/218,114

(22) Filed: Jul. 11, 2008

(65) Prior Publication Data

US 2008/0287691 A1  Nov. 20, 2008

Related U.S. Application Data

(63) Continuation of application No. 09/714,351, filed on Nov. 16, 2000, now Pat. No. 7,411,075.

(60) Provisional application No. 60/166,152, filed on Nov. 17, 1999.

(51) Int. Cl.
C07D 207/34 (2006.01)
A61K 31/40 (2006.01)

(52) U.S. Cl. .................................. 548/537; 514/423
(58) Field of Classification Search .................. 548/537
See application file for complete search history.

(56) References Cited

U.S. PATENT DOCUMENTS

| | | | |
|---|---|---|---|
| 4,137,322 A | 1/1979 | Endo et al. | |
| 4,681,893 A | 7/1987 | Roth | |
| 5,003,080 A | 3/1991 | Butler et al. | |
| 5,273,995 A | 12/1993 | Roth | |
| 5,298,627 A | 3/1994 | Butler et al. | |
| 5,686,104 A | 11/1997 | Mills et al. | |
| 5,969,156 A | 10/1999 | Briggs et al. | |
| 6,087,511 A | 7/2000 | Lin et al. | |
| 6,121,461 A | 9/2000 | McKenzie | |
| 6,476,235 B2 | 11/2002 | Butler et al. | |
| 6,528,661 B2 | 3/2003 | Niddam et al. | |
| 6,531,507 B1 | 3/2003 | Pflaum et al. | |
| 6,600,051 B2 | 7/2003 | Tully | |
| 6,605,636 B2 | 8/2003 | Aronhime et al. | |
| 6,605,728 B2 | 8/2003 | O'Connell et al. | |
| 6,605,729 B1 | 8/2003 | Byrn et al. | |
| 6,806,290 B2 | 10/2004 | Pflaum et al. | |
| 7,144,916 B2 | 12/2006 | Aronhime et al. | |
| RE39,502 E | 3/2007 | Fox et al. | |
| 2002/0099224 A1 | 7/2002 | Niddam et al. | |
| 2002/0115709 A1 | 8/2002 | Aronhime et al. | |
| 2003/0114686 A1 | 6/2003 | Van Der Schaaf et al. | |
| 2003/0212279 A1 | 11/2003 | Tessler et al. | |
| 2003/0216584 A1 | 11/2003 | Aronhime et al. | |
| 2004/0054193 A1 | 3/2004 | Byrn et al. | |
| 2004/0077708 A1 | 4/2004 | Grahek et al. | |
| 2004/0106670 A1 | 6/2004 | Blatter et al. | |
| 2004/0220255 A1 | 11/2004 | Van Der Schaaf et al. | |
| 2004/0242899 A1 | 12/2004 | Reddy et al. | |
| 2005/0209306 A1 | 9/2005 | Jegorov et al. | |

FOREIGN PATENT DOCUMENTS

| | | |
|---|---|---|
| EP | 0 247 633 A1 | 12/1987 |
| EP | 0 409 281 A1 | 1/1991 |
| HU | P9900678 | 7/1999 |
| WO | WO 94 16693 | 8/1994 |
| WO | WO 97/03958 | 2/1997 |
| WO | WO 97 03958 | 2/1997 |
| WO | WO 97/03959 | 2/1997 |
| WO | WO 97/03960 | 2/1997 |
| WO | WO 00/71116 A | 11/2000 |
| WO | WO 01/28999 A | 4/2001 |
| WO | WO 01/36384 | 5/2001 |
| WO | WO 01/42209 A | 6/2001 |
| WO | WO 01/44180 | 6/2001 |
| WO | WO 01/44181 | 6/2001 |
| WO | WO 02/41834 | 5/2002 |
| WO | WO 02/43732 | 6/2002 |
| WO | WO 02/051804 | 7/2002 |
| WO | WO 02/057228 | 7/2002 |
| WO | WO 02/057229 | 7/2002 |
| WO | WO 02/059087 | 8/2002 |
| WO | WO 02/083637 | 10/2002 |
| WO | WO 02/083638 | 10/2002 |
| WO | WO 03/004470 | 1/2003 |
| WO | WO 03/011826 | 2/2003 |
| WO | WO 03/016317 A | 2/2003 |

(Continued)

OTHER PUBLICATIONS

Thomas M.A. Bocan et al. "Antiatherosclerotic activity of inhibitors of 3-hydroxy-3-methylglutaryl coenzyme A reductase in cholesterol-fed rabbits: a biochemical and morphological evaluation", Atheroselerosis 111 (1994) pp. 127-142.

Thomas M.A. Bocan, Declaration Under Rule 132, dated Dec. 2, 1998, filed in U.S. Appl. No. 08/945,812; 2 pages.

Stephen R. Byrn, Declaration Under Rule 132, dated Nov. 25, 1998, filed in U.S. Appl. No. 08/945,812; 3 pages.

David J. W. Grant, Theory and Origin of Polymorphism, in Drugs of the Pharmaceutical Sciences, vol. 95, Polymorphism in Pharmaceutical Solids, Chapter 1, (Harry G. Brittain ed., 1999).

(Continued)

*Primary Examiner*—Laura L. Stockton
(74) *Attorney, Agent, or Firm*—Kenyon & Kenyon LLP

(57) ABSTRACT

The present invention relates to atorvastatin calcium, a useful agent for lowering serum cholesterol levels. New atorvastatin calcium Form V, processes for preparing the new form, and pharmaceutical compositions and dosage forms containing the new form are disclosed.

7 Claims, 2 Drawing Sheets

FOREIGN PATENT DOCUMENTS

| WO | WO 03/018547 | 3/2003 |
|---|---|---|
| WO | WO 03/050085 | 6/2003 |
| WO | WO 03/070702 | 8/2003 |
| WO | WO 2004/022053 | 3/2004 |
| WO | WO 2004/050618 | 6/2004 |

OTHER PUBLICATIONS

K.L. Baumann et al., "The Convergent Synthesis of CI-981, an Optically Active, Highly Potent, Tissue Selective Inhibitor of HMG-CoA Reductase," Tetrahedron Letters, vol. 33, No. 17 (1992) pp. 2283-2284.

Goodman and Gilman's The Pharmacological Basis of Therapeutics, 9th Ed. (1996) pp. 879-881.

Cheronis, Semimicro Experimental Organic Chemistry, pp. 31-49.

Haleblian & Crone, 1969. J. Pharm. Sci.58:911-929.

G. Michael Wall, "Pharmaceutical Applications of Drug Crystal Studies", Pharmaceutical Manufacturing (Feb. 1986) pp. 33-42.

U.S. Pharmacopia #23, p. 1843, 941 X-Ray Diffraction, 1995.

McCrone W.C., "Polymorphism", Physics and Chemistry of the Organic Solid State, vol. 2, 1965, pp. 725-767.

Caira M.R., "Crystalline Polymorphism of Organic Compounds" Topics in Current Chemistry, Springer, Berlin, DE, vol. 198, 1998, pp. 163-208.

Graul A., et al., "Atorvastatin Calcium" Drugs of the Future, Barcelona, ES, vol. 22, No. 9, 1997, pp. 956-968.

Guillory, J.K.: "in Polymorphism in Pharmaceutical Solids (Brittain, H.G., ed.)", 1999, Marcel Dekker, Inc., New York, Basel, pp. 183-226.

Hancock B.C., et al., "Characteristics and Significance of the Amorphous State in Pharmaceutical Systems", Journal of Pharmaceutical Sciences, American Pharmaceutical Association, Washington, U.S., vol. 86, No. 1, Jan. 1997, pp. 1-12.

Walter DeGruyter, Concise Encyclopedia Chem. (1993), Berlin, NY, Title page and copyright page only.

Bernstein, J. (2002) "Polymorphism in Molecular Crystals," pp. 1-28 and 240-256 (Clarendon Press, Oxford, U.K., pub.).

Brittain, H.G. ed.(1999) "Methods for the Characterization of Polymorphs and Solvates," pp. 227-240 in "Polymorphism in Pharmaceutical Solids" (Brittain, H.G., ed., Marcel Dekker, Inc., New York, NY, pub.).

Brittain, H.G., ed. (1999) "Methods for the Characterization of Polymorphs and Solvates," pp. 1-3, 178-179, 185-187, 219, 236 in "Polymorphism in Pharmaceutical Solids" (Marcel Dekker, Inc., New York, NY, pub.).

Brittain, H.G., ed. (1999) "Generation of Polymorphs, Hydrates, Solvates, and Amorphous Solids," pp. 183-226 in "Polymorphism in Pharmaceutical Solids" (Marcel Dekker, Inc., New York, NY, pub.).

Brittain, H.G., ed. (1999) "Methods for the Characterization of Polymorphs and Solvates," pp. 348-361 in "Polymorphism in Pharmaceutical Solids" (Marcel Dekker, Inc., New York, NY, pub.).

Byrn, S.R., et al., (1999) "Drugs as Molecular Solids," pp. 3-5 in "Solid-State Chemistry of Drugs," 2nd ed., (SSCI, Inc., West Lafayette, IN, pub.).

Byrn, S.R., et al. (1999) "The X-Ray Powder Diffraction Method," pp. 59-63 in "Solid-State Chemistry of Drugs" 2nd ed., (SSCI, Inc., West Lafayette, IN, pub.).

Chen, B., et al., "Synthesis of Deuterium-Labeled Atorvastatin and its Metabolites for Use as Internal Standards in a LC/MS/MS Method Developed for Quantitation of the Drug and its Metabolites in Human Serum," Journal of Labeled Compounds and Radiopharmaceuticals 43 (2000) pp. 261-270.

POLYMORPHIC FORM OF ATORVASTATIN CALCIUM

CROSS-REFERENCE TO RELATED APPLICATIONS

This application is a continuation of application Ser. No. 09/714,351 filed Nov. 16, 2000, now U.S. Pat. No. 7,411,075 which claims the benefit of provisional application Ser. No. 60/166,152, filed Nov. 17, 1999, the contents of all of which are incorporated herein by reference.

FIELD OF THE INVENTION

The present invention relates to a novel crystalline form of atorvastatin calcium, to processes for preparing it and to pharmaceutical compositions and dosages containing it.

BACKGROUND OF THE INVENTION

Atorvastatin is a member of the class of drugs called statins. Statin drugs are currently the most therapeutically effective drugs available for reducing low density lipoprotein (LDL) particle concentration in the blood stream of patients at risk for cardiovascular disease. A high level of LDL in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and patients who are free of cardiovascular disease but who have hypercholesterolemia. Scandinavian Simvastatin Survival Study Group, 1994; Lipid Research Clinics Program, 1984a, 1984b.

The mechanism of action of statin drugs has been elucidated in some detail. They interfere with the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion HMG to mevalonate, which is the rate determining step in the biosynthesis of cholesterol, and so, its inhibition leads to a reduction in the concentration of cholesterol in the liver. Very low density lipoprotein (VLDL) is the biological vehicle for transporting cholesterol and triglycerides from the liver to peripheral cells. VLDL is catabolized in the peripheral cells which releases fatty acids which may be stored in adipocytes or oxidized by muscle. The VLDL is converted to intermediate density lipoprotein (IDL), which is either removed by an LDL receptor, or is converted to LDL. Decreased production of cholesterol leads to an increase in the number of LDL receptors and corresponding reduction in the production of LDL particles by metabolism of IDL.

Atorvastatin is the common chemical name of [R—(R*, R*)]-2-(4-fluorophenyl)-β,δ-dihydroxy-5-(1-methylethyl)-3-phenyl-4-[(phenylamino)carbonyl]-1H-pyrrole-1-heptanoic acid. The free acid is prone to lactonization. The molecular structure of the lactone is represented by formula (I).

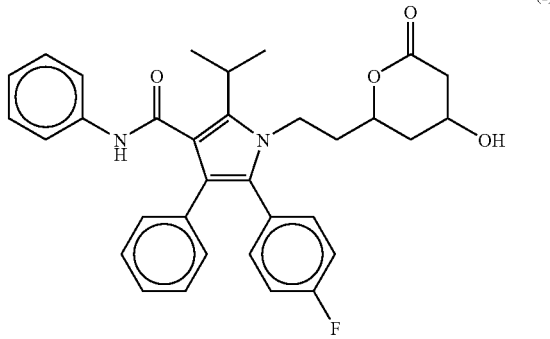

(I)

Atorvastatin is marketed as the hemi calcium salt-trihydrate under the name LIPITOR by Warner-Lambert Co.

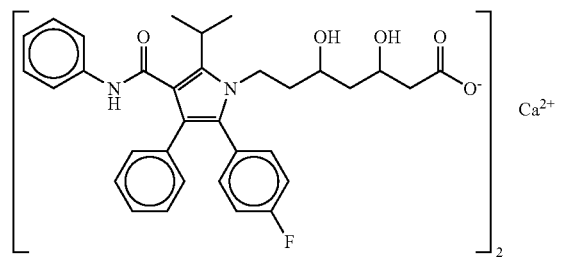

(II)

Atorvastatin was first disclosed to the public and claimed in U.S. Pat. No. 4,681,893. The hemi calcium salt depicted in formula (II) (hereafter "atorvastatin calcium") is disclosed in U.S. Pat. No. 5,273,995. This patent teaches that the calcium salt is obtained by crystallization from a brine solution resulting from the transposition of the sodium salt with $CaCl_2$ and further purified by recrystallization from a 5:3 mixture of ethyl acetate and hexane. Both of these U.S. patents are hereby incorporated by reference.

The present invention includes a new crystal form of atorvastatin calcium in both hydrate and anhydrate states. Polymorphism is the property of some molecules and molecular complexes to assume more than one crystalline or amorphous form in the solid state. A single molecule, like the atorvastatin in formula (I) or the salt complex of formula (II), may give rise to a variety of solids having distinct physical properties like solubility, X-ray diffraction pattern and solid state $^{13}C$ NMR spectrum. The differences in the physical properties of polymorphs result from the orientation and intermolecular interactions of adjacent molecules (complexes) in the bulk solid. Accordingly, polymorphs are distinct solids sharing the same molecular formula, which may be thought of as analogous to a unit cell in metallurgy, yet having distinct advantageous and/or disadvantageous physical properties compared to other forms in the polymorph family. One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. On the other hand, where the effectiveness of a drug correlates with peak bloodstream levels of the drug, a property shared by statin drugs, and provided the drug is rapidly absorbed by the GI system, then a more rapidly dissolving form is likely to exhibit increased effectiveness over a comparable amount of a more slowly dissolving form.

U.S. Pat. No. 5,969,156 discloses three polymorphs of atorvastatin designated Forms I, II, and IV by the inventors of those forms. While the inventors of U.S. Pat. No. 5,969,156 claim certain processing and therapeutic advantages of their forms over amorphous atorvastatin calcium, advantages may yet be realized by other heretofore undiscovered forms of atorvastatin calcium.

SUMMARY OF THE INVENTION

The present invention provides new Form V of atorvastatin calcium in both anhydrate and hydrate states, which possesses the advantage of higher solubility in water than atorvastatin Form I. The present invention further provides a process for preparing new Form V as well as pharmaceutical compositions and dosages containing the new form.

DETAILED DESCRIPTION OF THE INVENTION

Figure 1:
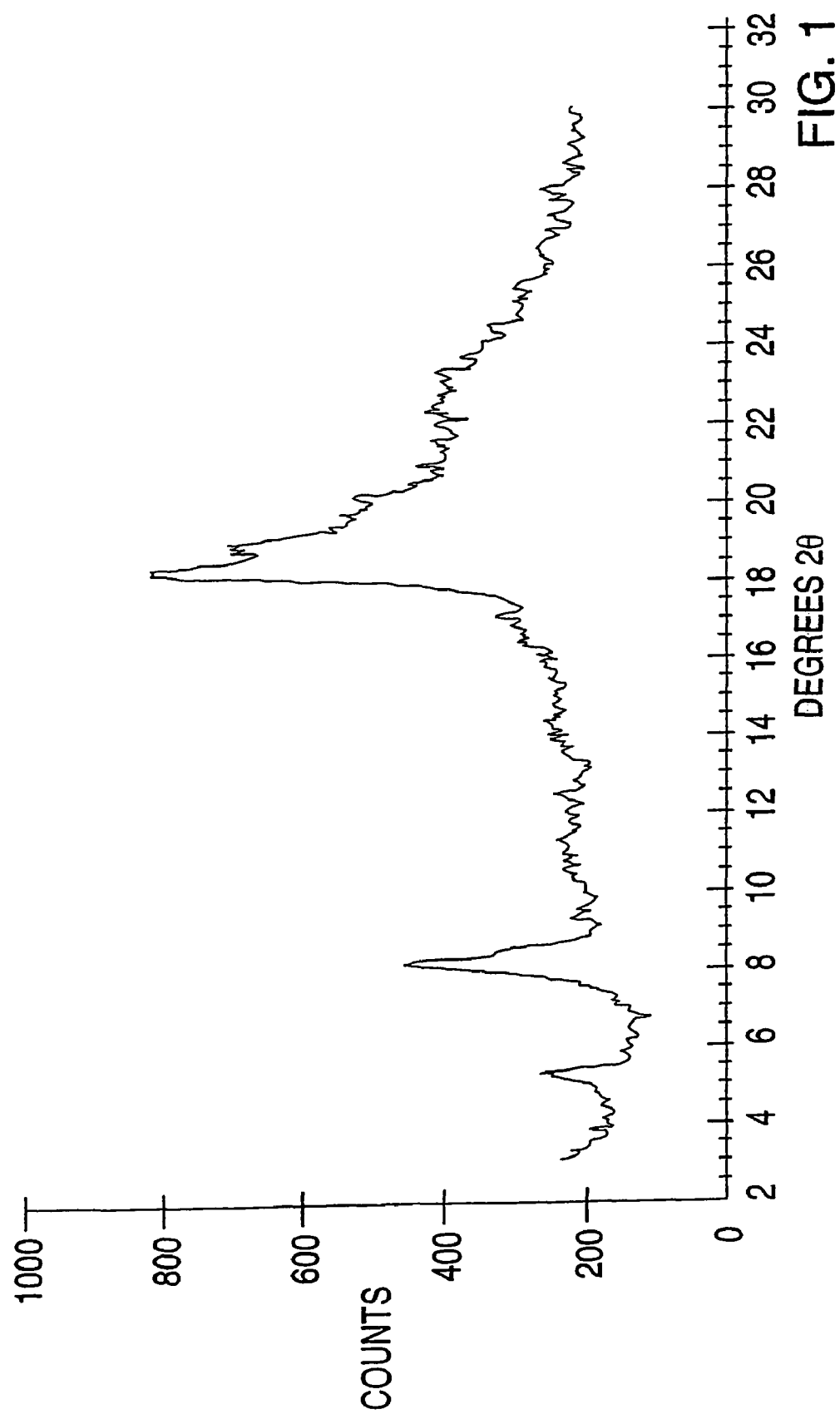
FIG. 1 is an X-ray powder diffractogram of atorvastatin calcium Form V.

The new crystalline form of atorvastatin calcium Form V is well distinguished from the crystal modifications obtained by carrying out the procedures described in U.S. Pat. Nos. 5,273,995 and 5,969,156 using X-ray powder diffraction and solid-state $^{13}C$ nuclear magnetic resonance techniques.

The X-ray powder diffractogram of Form V (FIG. 1) has two medium peaks at 5.3±0.2 and 8.3±0.2 degrees 2θ and one large peak in the range 18-23 degrees 2θ with a maximum at about 18.3±0.2 degrees two-theta. This X-Ray pattern is well distinguished from that of known Forms I, II, III and IV and also is well distinguished from the X-Ray pattern of amorphous atorvastatin calcium which is characterized by two broad humps in the ranges 8-14 degrees 2θ and 15-26 degrees 2θ. The X-ray powder diffractogram of FIG. 1 was obtained by methods known in the art using a Philips X-ray powder diffractometer with a curved graphite monochromator using goniometer model 1050/70. Copper radiation of λ=1.5418 Å was used. Measurement range: 3-30 degrees 2θ.

The solid-state $^{13}C$ NMR spectrum of Form V is characterized by the following chemical shifts:

| δ (ppm) | |
|---|---|
| 21.9 | |
| 25.9 | |
| 40.4 | |
| 41.8 | |
| 42.3 | |
| 63-73 | (two broad peaks) |
| 115.6 | |
| 118.9 | |
| 122.5 | |
| 128.7 | (strong) |
| 135.1 | |
| 161.0 | |
| 167.1 | |
| 176-186 | (broad peak) |

This solid-state $^{13}C$ NMR spectrum (FIG. 2) is well distinguished from those of known Forms I, II, III and IV, and also is distinguished from that of the amorphous form which displays a different pattern with shifts significantly different from that of Form V at 21.0 ppm, 26.4 ppm, one broad peak in the range 60-75 ppm with a maximum at 69.7 ppm and 138.8 ppm. The spectrum of FIG. 2 was obtained on a Bruker DMX-500 digital F NMR spectrometer operating at 125.76 MHz. The instrument was equipped with a BL -4 cpmas probehead and a high resolution/high performance (HPHP) $^{1}H$ for solids. The magic angle and proton decoupling efficiency were optimized before acquisition. The sample was spun at 5.0 kHz spin rate on 4 mm zirconia rotors.

Atorvastatin calcium Form V may contain up to 12% water, which corresponds to the stoichiometric value of 9 water molecules per molecule of atorvastatin calcium. Thus, atorvastatin calcium Form V can be in various states of hydration, between 0 and 9 moles of water.

The present invention further provides a process for the preparation of atorvastatin calcium Form V. The process comprises the steps of dissolving a salt of atorvastatin in a solvent to form an atorvastatin salt solution, optionally removing impurities from the atorvastatin salt solution, contacting the atorvastatin salt solution with a calcium salt and isolating atorvastatin calcium in new Form V.

The atorvastatin salt of the present invention includes alkali metal salts, e.g. lithium, sodium, and potassium salts; alkaline-earth metal salts such as magnesium salts; as well as ammonium and alkyl, aryl or alkaryl ammonium salts. The preferred atorvastatin salts are alkali metal salts; most preferred is the sodium salt.

Any solvent capable of dissolving the atorvastatin salt and from which atorvastatin calcium Form V may be isolated is a suitable solvent of the invention. The choice of solvent will therefore depend upon the selection of the atorvastatin salt and the calcium salt. The solvent should be selected from those in which the atorvastatin salt and calcium salt are at least sparingly soluble. By sparingly soluble is meant not substantially less soluble than 0.02 g/ml at 50-60° C. for the atorvastatin salt and not substantially less soluble than 0.0002 M at 10-15° C. for the calcium salt.

Suitable solvents include but are not limited to hydroxylic solvents like water, alcohols and mixtures thereof, including hydroxylic solvents and hydroxylic solvent mixtures which have been made either acidic or basic by addition of a mineral acid or base. Preferred solvents are water, methanol, ethanol and mixtures thereof.

The calcium salt of the present invention includes organic and inorganic salts of calcium which are capable of dissociating into $Ca^{2+}$ and an anionic component when added to the atorvastatin salt solution. Among the organic salts that may be used are carboxylates and sulfonates. Among the carboxylates are lower alkyl carboxylates like acetate, proprionate, butyrate and tartrate and aryl carboxylates like benzoate and phthalate as well as higher alkyl carboxylates like stearate, dodecanoate and the like. Also included are calcium ascorbate and succinate. Among the sulfonates that may be used are lower alkyl and aryl sulfonates like calcium methane sulfonate, calcium benzene sulfonate and calcium p-toluene sulfonate. The preferred organic calcium salts are lower carboxylate salts, the most preferred organic calcium salt is calcium acetate.

Depending upon solubility, inorganic salts which may be used include halide salts such as $CaCl_2$, $CaF_2$, $CaBr_2$ and $CaI_2$, as well as calcium borate ($B_4CaO_7$), calcium tetrafluoroborate ($CaBF_4$), calcium carbonate ($CaCO_3$), monobasic calcium phosphate ($Ca(H_2PO_4)_2$), dibasic calcium phosphate (CaHPO$_4$) and tribasic calcium phosphate (Ca(PO$_4$)$_2$), calcium sulfate (CaSO$_4$) and calcium hydroxide (Ca(OH)$_2$), and hydrates thereof.

Whether organic or inorganic, the calcium salt is preferably added in an amount that provides one half mole of Ca$^{2+}$ per mole of atorvastatin in the atorvastatin salt solution. For example, if the atorvastatin salt is atorvastatin sodium (atorvastatin$^-$ Na$^+$), then about one half mole of calcium salt per mole of the atorvastatin salt is appropriate. If the atorvastatin salt is atorvastatin magnesium ([atorvastatin$^-$]$_2$ Mg$^{2+}$), then about one mole of calcium salt per mole of atorvastatin salt is appropriate. Otherwise, mixed salts containing atorvastatin may form.

The calcium salt may be contacted with the atorvastatin salt solution by adding the calcium salt in substantially pure form, i.e. either as a solid or, if liquid, as a neat liquid, to the atorvastatin salt solution or, preferably, by first forming a calcium salt solution and then contacting the atorvastatin salt solution and calcium salt solution. It is most preferred to contact the calcium salt and the atorvastatin salt solution by first dissolving the calcium salt in a solvent and then adding the calcium salt solution to the atorvastatin salt solution slowly. Suitable calcium salt solvents are solvents previously mentioned as being suitable solvents for the atorvastatin salt, provided the calcium salt is at least sparingly soluble in the particular solvent.

In a particularly preferred embodiment, wherein the atorvastatin salt is an atorvastatin alkali metal salt and the atorvastatin salt solvent is a 1:2 methanol:water mixture, the preferred calcium salt is calcium acetate and the preferred calcium salt solvent is water. When the calcium salt solvent is water, it is preferably used in an amount that provides about a 20 to 30 millimolar solution of the calcium salt, more preferably about a 25 millimolar solution.

In addition, the atorvastatin and calcium salts are preferably combined at elevated temperature and at concentrations disclosed above and in the examples, which follow, in order that crystallization of Form V may be induced by cooling of the so-formed atorvastatin calcium solution. The elevated temperature is preferably above 40° C. and below 80° C., more preferably above 50° C. and below 70° C. and most preferably about 60° C. One skilled in the art will appreciate that by adjusting temperature and concentration, the yield of atorvastatin calcium Form V may be optimized. Crystallization of atorvastatin calcium Form V may also be induced by addition of a seed crystal of atorvastatin calcium, preferably Form V although other forms also may be used.

Once crystals of atorvastatin Form V have crystallized, either spontaneously, upon cooling, upon seeding or by another inducement, the crystals may be isolated by filtration or other conventional means known to the art. The isolated crystals may also be dried by conventional means.

It has also been found that atorvastatin calcium can be crystallized in Form V by dissolving atorvastatin calcium in THF or alcohols like methanol or ethanol, and subsequently adding water as an antisolvent.

A further aspect of the present invention is a pharmaceutical composition and dosage form containing the novel form of atorvastatin calcium.

The compositions of the invention include powders, granulates, aggregates and other solid compositions comprising novel Form V of atorvastatin calcium. In addition, Form V solid compositions that are contemplated by the present invention may further included diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that may also be present in a solid composition of Form V atorvastatin calcium further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The Dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of atorvastatin calcium whereupon the properties that distinguish the solid forms of atorvastatin calcium are lost. However, the use of the novel forms to prepare such solutions (e.g. so as to deliver, in addition to atorvastatin, a solvate to said solution in a certain ratio with a solvate) is considered to be within the contemplated invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred unit dosages of the pharmaceutical compositions of this invention typically contain from 0.5 to 100 mg of the novel atorvastatin calcium Form V, or mixtures thereof with other forms of atorvastatin calcium. More usually, the combined weight of the atorvastatin calcium forms of a unit dosage are from 2.5 mg. to 80 mg.

Having thus described the various aspects of the present invention, the following examples are provided to illustrate specific embodiments of the present invention. They are not intended to be limiting in any way.

EXAMPLES

Example 1

The sodium salt of atorvastatin (52.2 g) was dissolved in methanol (510 ml) and then diluted with water (1 L). The resulting solution was transferred to a separatory funnel containing 1:1 ethyl acetate/hexane (1 L). The phases were mixed by bubbling nitrogen gas through the separatory funnel. Upon cessation of nitrogen flow, the phases separated and the upper, organic, phase was removed. The lower, aqueous, phase was washed with 1:1 ethyl acetate/hexane (1 L) and then transferred to a round bottom flask. Active charcoal (10.2 g) was added. The flask was heated to 50° C. and the solution was stirred for two hours. The activated charcoal was then removed by filtration through celite, the charcoal and celite being rinsed with methanol (1540 ml), and the rinsate and filtrate then being combined into one atorvastatin sodium salt solution.

The quantity of atorvastatin obtained by purification was determined by calibrated HPLC analysis of the purified atorvastatin sodium salt solution. Based on this analysis, a quantity of calcium acetate (8.38 g, 0.5 eq.) was dissolved in water (1.9 L) and heated to 60° C. The atorvastatin sodium salt solution was heated to 63° C. and the solutions were combined by slow addition of the calcium acetate solution to the atorvastatin sodium salt solution. Upon completing the addition, the mixture was cooled. Crystallization of Form V began to occur at a temperature of 43° C. and cooling was continued until the flask temperature reached 13° C.

The crystals were isolated by slow vacuum filtration and then dried over anhydrous silica for 5 days to yield atorvastatin calcium salt Form V.

Example 2

Atorvastatin calcium (10 g) was dissolved in methanol (400 ml) at room temperature. Water (300 ml) was added slowly to the methanolic solution with stirring and the resulting solution was heated to 60° C. The solution was then cooled to between 10 and 15° C. within 3 h. Precipitation started at about 40° C. The thick slurry was then dried at 50° C. under reduced pressure for 48 h to yield atorvastatin calcium Form V.

Example 3

Atorvastatin calcium (5 g) was dissolved in methanol (100 ml) at room temperature. To this methanolic solution, water (100 ml) was added while stirring. Precipitation occurred instantly and after cooling the slurry to 15° C. the precipitate was filtered and dried at 50° C. under reduced pressure for 48 h to yield atorvastatin calcium Form V.

Example 4

Atorvastatin calcium (5 g) was dissolved in methanol (200 ml). The methanolic solution was placed into a stirred reactor containing water (150 ml) at 45° C. The obtained slurry was cooled to 10° C., filtered and dried at 50° C. under reduced pressure for 48 h to yield atorvastatin calcium Form V.

Example 5

Atorvastatin calcium (1 g) was dissolved in ethanol (15 ml) after heating. To this ethanolic solution, water (10 ml) was added while stirring. Precipitation occurred instantly. The gel-like precipitate was filtered without vacuum and dried at 50° C. under reduced pressure for 24 h to yield atorvastatin calcium Form V.

Example 6

Atorvastatin calcium (1 g) was dissolved in THF (25 ml) at room temperature. To this solution, water (60 ml) was added while stirring. The reaction mixture was stirred for 18 hours at room temperature and the precipitate (gel) was filtered without vacuum and dried at 50° C. under reduced pressure for 24 h to yield atorvastatin calcium Form V.

The invention has been described with reference to its preferred embodiments. From this description, those skilled in the art may appreciate changes that could be made in the invention which do not depart from the scope and spirit of the invention as described above and claimed hereafter.

Figure 2:
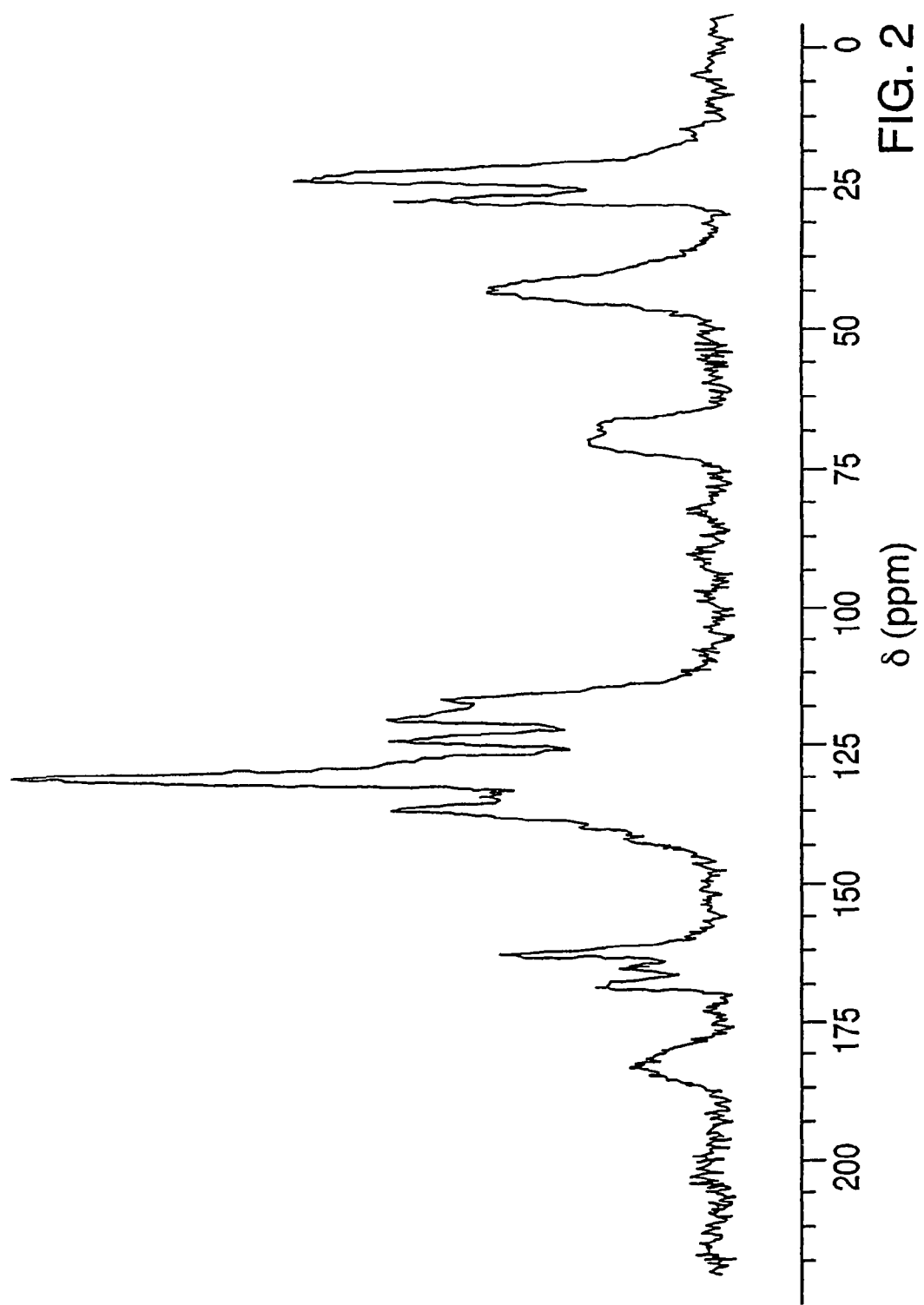
FIG. 2 is a solid state $^{13}C$ NMR spectrum of atorvastatin calcium Form V.

We claim:

1. A pharmaceutical composition that is a solid or suspension comprising atorvastatin calcium Form V having an X-ray powder diffractogram substantially as depicted in FIG. 1 or having a solid state $^{13}C$ NMR spectrum substantially as depicted in FIG. 2.

2. A pharmaceutical composition that is a solid or suspension comprising atorvastatin calcium Form V characterized by X-ray powder diffraction peaks at 5.3±0.2 and 8.3±0.2 degrees 2θ and a broad peak at 18-23±0.2 degrees 2θ with a maximum at 18.3-±0.2 degrees 2θ.

3. A pharmaceutical composition that is a solid or suspension comprising atorvastatin calcium Form V characterized by $^{13}C$ NMR signals at 21.9, 25.9, 118.9, 122.5, 128.7, 161.0 and 167.1 ppm.

4. The pharmaceutical composition of claim 1 where Form V is produced by a process comprising the steps of
   a) dissolving a metal, ammonium or alkylammonium salt of atorvastatin in a solvent to form an atorvastatin salt solution,
   b) contacting the atorvastatin salt solution with a calcium salt,
   c) isolating crystalline atorvastatin calcium Form V, and
   d) preparing a pharmaceutical composition containing the isolated crystalline atorvastatin calcium Form V.

5. The pharmaceutical composition of claim 1 comprising a therapeutic amount of atorvastatin calcium Form V.

6. The pharmaceutical composition of claim 2 comprising a therapeutic amount of atorvastatin calcium Form V.

7. The pharmaceutical composition of claim 3 comprising a therapeutic amount of atorvastatin calcium Form V.

* * * * *